United States Patent [19]

Nash

[11] Patent Number: 4,720,555

[45] Date of Patent: Jan. 19, 1988

[54] HYDROCARBYL ANHYDRIDES

[75] Inventor: William D. Nash, The Woodlands, Tex.

[73] Assignee: Pennzoil Products Company, Houston, Tex.

[21] Appl. No.: 907,144

[22] Filed: Sep. 12, 1986

[51] Int. Cl.$^4$ ............................................. C07D 307/60
[52] U.S. Cl. ..................................... 549/252; 106/270; 106/271
[58] Field of Search ....................... 549/252, 233, 255; 106/270, 271

[56] References Cited

U.S. PATENT DOCUMENTS

| | | | |
|---|---|---|---|
| 2,993,773 | 7/1961 | Stromberg | 52/0.5 |
| 3,030,387 | 4/1962 | Benoit, Jr. | 260/346.8 |
| 3,045,042 | 7/1962 | Staker | 260/485 |
| 3,231,498 | 1/1966 | de Vries | 252/56 |
| 3,255,108 | 6/1966 | Wiese | 252/32.7 |
| 3,381,022 | 4/1968 | Le Suer | 260/404.8 |
| 3,428,561 | 2/1969 | Lesuer | 252/32.5 |
| 3,449,236 | 6/1969 | Engelhart | 208/28 |
| 3,579,453 | 5/1971 | Dupre et al. | 252/89 |
| 3,590,076 | 6/1971 | Heintzelman et al. | 260/485 |
| 3,640,872 | 2/1972 | Wiley et al. | 252/75 |
| 3,694,176 | 9/1972 | Miller | 44/62 |
| 3,833,502 | 9/1974 | Leary et al. | 252/49.5 |
| 3,923,669 | 12/1975 | Newingham et al. | 252/33 |
| 3,957,854 | 5/1976 | Miller | 252/40.5 |
| 4,012,438 | 3/1977 | Lavigne | 549/252 |
| 4,036,772 | 7/1977 | Dorer, Jr. | 252/56 R |
| 4,041,056 | 8/1977 | Heintzelman et al. | 260/404.5 |
| 4,086,251 | 4/1978 | Cengel et al. | 260/346.74 |
| 4,256,605 | 3/1981 | Baker | 252/312 |
| 4,315,863 | 2/1982 | Tomoshige et al. | 549/233 |
| 4,368,133 | 1/1983 | Forsberg | 252/75 |
| 4,440,902 | 4/1984 | Diery et al. | 525/404 |
| 4,447,348 | 5/1984 | Forsberg | 252/75 |
| 4,450,281 | 5/1984 | Wollenberg | 549/255 |
| 4,481,125 | 11/1984 | Holgado | 252/75 |
| 4,486,324 | 12/1984 | Korosec | 252/75 |
| 4,504,275 | 3/1985 | Baker | 44/51 |
| 4,504,276 | 3/1985 | Baker | 44/51 |
| 4,509,950 | 4/1985 | Baker | 44/51 |
| 4,554,080 | 11/1985 | Headley | 252/8.5 A |

*Primary Examiner*—Henry R. Jiles
*Assistant Examiner*—Bernard I. Dentz
*Attorney, Agent, or Firm*—Lowe, Price, Leblanc, Becker & Shur

[57] ABSTRACT

Hydrocarbons substituted with at least two anhydride moieties, are useful as dispersants in aqueous based hydraulic fluids and as curing agents in epoxy resins. These anhydrides are produced by reaction of a hydrocarbon derived from a soft wax or liquid hydrocarbon with a molar excess of an organic anhydride, preferably using a molar ratio excess of 3:1 to 8:1 of maleic anhydride, and under free radical conditions. The products are insoluble in the parent hydrocarbons.

3 Claims, No Drawings

HYDROCARBYL ANHYDRIDES

FIELD OF THE INVENTION

This invention relates to novel hydrocarbons, substituted with multiple succinic anhydride groups and produced by reaction of hydrocarbons and maleic anhydride, and more particularly to such novel anhydrides and their use in hydraulic fluid compositions and as epoxy resin curing agents.

BACKGROUND

The patent literature is replete with disclosures for the preparation and use of alkyl succinic anhydrides. There are disclosures with regard to reaction products of succinic anhydrides with various alkyl moieties including wax, paraffins and the like. For example, U.S. Pat. No. 4,041,056 discloses wax anhydride compounds and uses in carbon paper, inks, polishes and the like. U.S. Pat. No. 3,449,236 discloses wax-maleic anhydride reaction products and use as dewaxing aids in separation wax from petroleum oil. U.S. Pat. No. 2,231,498 describes lubricants which contain alkyl substituted succinic acid compounds which are produced as the maleic anhydride adduct of a high molecular weight unsaturated hydrocarbon polymer. U.S. Pat. No. 4,486,324 describes hydraulic fluids which contain a hydrocarbyl substituted succinic acid which is produced by reacting an olefinically unsaturated aliphatic hydrocarbon with maleic anhydride which is then hydrolyzed to form the acid. U.S. Pat. Nos. 4,554,080, 3,923,669, 3,428,561, 4,450,281, and 4,086,251 all disclose alkyl or alkenyl substituted anhydrides which are produced by the reaction of maleic anhydride with a hydrocarbon and their use in hydraulic oils and hydraulic fluids. U.S. Pat. Nos. 3,030,387 and 3,590,076 specifically describe wax-anhydride reaction products. U.S. Pat. No. 4,041,056, mentioned above, also describes reaction products of wax anhydride compounds, together with further reaction with polyamines. Both U.S. Pat. Nos. 4,041,056 and 3,590,076 refer to U.S. Pat. No. 3,030,387 as describing the basic process for preparation of such products. As disclosed in U.S. Pat. No. 3,030,387, these products are produced by reaction of an alkane or cycloalkane with maleic anhydride in the presence of a peroxide free-radical initiator catalyst. Excess alkane or cycloalkane is ordinarily employed in up to a ten fold in molar excess in order to ensure as complete reaction as possible. The working examples support this manner of carrying out the reaction. U.S. Pat. Nos. 4,041,056 and 3,590,076 are directed to coupling of these materials with polyfunctional poly alcohols in U.S. Pat. No. 3,590,076 and with polyamines in U.S. Pat. No. 4,041,056. Both of these patents present general structural formulae in column 1 for products which are said to be representative of the wax-anhydride compounds produced according to this process. However, the present invention differs in several important respects: (A) Both U.S. Pat. Nos. 4,041,056 and 3,590,076 state in column 3 that liquids and soft solids do not yield the products of their respective inventions. Further, both cited patents state in their first claim that the wax reactant has a melting point of at least 150° F. and a penetration of from 0+ to about 50. The present invention pertains only to liquid, soft solid, and waxy hydrocarbons melting below 150° F. While U.S. Pat. No. 3,030,387 teaches liquid and low melting hydrocarbon reactants, it pertains to and claims only monoanhydride products, obtained with excess molar ratios of hydrocarbon. (B), Both U.S. Pat. Nos. 4,041,056 and 3,590,076 teach in their examples, Tables 1 and 2, and first claims, the use of maleic anhydride to wax mole ratios of 1.5 or less. The present invention pertains only to higher maleic anhydride to wax mole ratios. (C), Table 1 of both patents teaches products with acid numbers of less than 50. The present invention pertains generally to products with acid numbers above 400. (D) Both patents teach in column 3 wax-soluble, methanol-insoluble products. The products of the present invention are insoluble in wax and soluble in polar solvents such as methanol, acetone, and aqueous solutions.

The present invention provides polyanhydrides produced by the reaction of maleic anhydride or equivalent anhydrides with long chained hydrocarbons, which polyanhydrides are distinguished from and advantageous over the prior art products discussed above. The terms "polyanhydride" or "polysuccinic anhydrides" as used herein, refer to multiple succinic anhydride groups substituted onto a hydrocarbon and are not to be confused with polymer connotations. By virtue of the excellent characteristics of the products of this invention, the solubility properties and physical form distinguish the products from the prior art and make such products advantageous as emulsifiers, surfactants or dispersants in hydraulic fluid compositions and as epoxy resin curing agents.

SUMMARY OF THE INVENTION

It is accordingly one object of the present invention to provide a novel class of polyanhydride products which are useful as emulsifiers, surfactants or dispersants in hydraulic fluid compositions and as epoxy resin curing agents.

It is a further object of the invention to provide a novel class of polyanhydride products formed by the reaction of a long chained hydrocarbon reactant with a molar excess of maleic anhydride or equivalent anhydride.

A further object of the present invention is to provide a novel method for the production of hydrocarbyl polysuccinic anhydrides which comprises the reaction of a hydrocarbon with an excess of a maleic anhydride in the absence of a solvent.

Other objects and advantages of the present invention will become apparent as the description thereof proceeds.

In satisfaction of the foregoing objects and advantages, there is provided by this invention a hydrocarbyl polysuccinic anhydride wherein the hydrocarbyl moiety is a hydrocarbon chain containing at least 6 carbon atoms and is derived from a soft solid or liquid hydrocarbon, and said product contains at least 2 anhydride substituents randomly located on the carbon chain, said polyanhydride being insoluble in the hydrocarbon starting material from which it is produced.

Also provided by the present invention is a method for the preparation of a hydrocarbyl polysuccinic anhydride which comprises the reaction of a hydrocarbon with a molar excess of an organic anhydride in the presence of a peroxide initiator.

Further provided by the present invention is an aqueous based hydraulic fluid comprising as a dispersant, a hydrocarbyl polysuccinic anhydride wherein the hydrocarbon chain contains at least 6 carbon atoms and is derived from a soft solid or liquid hydrocarbon, and which product contains at least 2 anhydride substituents randomly located along the hydrocarbon chain, and said material being insoluble in the hydrocarbon starting material from which it is produced.

The present invention also provides epoxy curing agents which comprise hydrocarbyl succinic anhydrides wherein the hydrocarbon chain contains at least 6 carbon atoms and is derived from a soft solid or liquid hydrocarbon, and wherein there are at least 2 anhydride substituents randomly located along the hydrocarbon chain.

DESCRIPTION OF PREFERRED EMBODIMENTS

The present invention provides methods for the preparation of the new polyanhydrides which are useful as emulsifiers, surfactants or dispersants in aqueous hydraulic fluid compositions and as epoxy resin curing agents. The new products are alkyl polysuccinic anhydrides which may be described by the following general formula:

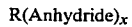

$$R(Anhydride)_x$$

wherein in the above formula, R is a hydrocarbyl group, anhydride is any organic anhydride, and x is an integer of at least 2 and preferably ranges from about 3 to about 8. The expression "hydrocarbyl" refers to a saturated hydrocarbon which may also contain unsaturation, aromatic rings, alkyl aromatics and alicyclic groups, and which have carbon chains which may be straight or branch-chained and contain at least 6 carbon atoms and preferably 6 to 100 carbon atoms. The hydrocarbyl groups are derived from hydrocarbons which are soft solids or waxes. The value for x denotes the number of anhydride groups attached to the hydrocarbyl chain.

The polyanhydrides of the present invention have physical and chemical properties which distinguish them from anhydrides of the prior art. The polyanhydrides of the invention are insoluble in the hydrocarbons from which they are made and thus are readily separable therefrom. The anhydrides are not describable by specific chemical structure, but rather are complex mixtures of hydrocarbyl, preferably alkyl chains, which contain anhydride groups randomly positioned along the carbon chain. The anhydride groups are attached as discrete units at various positions along the hydrocarbon chain and/or may be linked in multiple units to one another with one or both ends attached to the hydrocarbon. Preferably at least three anhydrides are attached along the hydrocarbon chain.

The alkylpolysuccinic anhydride products of the present invention perform satisfactorily as dispersants in high water content hydraulic fluid formulations. The polyahydride products exhibit excellent stability as dispersants in such formulations, even when used in hard water which contains up to 1500 ppm calcium carbonate.

The products of the invention are also useful as epoxy resin curing agents in combination with conventional epoxy resins.

According to this invention it has been discovered that the hydrocarbyl polyanhydrides of the present invention can be produced from neat hydrocarbons by treating the hydrocarbons with molar excesses of organic anhydride and a peroxide initiator. By the expression "neat hydrocarbons" it is intended to mean that no diluent is necessary for conducting the reaction but that direct reaction can be carried out between the hydrocarbons and the anhydride.

The present invention is described herein with reference to the reaction of alkane hydrocarbons with maleic anhydride in order to produce alkyl polysuccinic anhydrides. However, it is to be understood that the invention is inclusive of the use of any long chained hydrocarbon derived from a soft solid or liquid as a starting material and any organic anhydride, provided that the polyanhydride products are produced which have the characteristics described herein for the final products.

It is a particular feature of the present invention that a molar excess of the anhydride should be reacted with the hydrocarbon. Maleic anhydride is exemplified for conducting the reaction in this application as this is the most readily available anhydride for use. However, equivalent anhydrides could also be used. By expression "molar excess", it is meant that the molar ratio of anhydride to hydrocarbon for the reaction should be in the range of at least 2:1 and preferably range from about 3:1 to 10:1. It has been found according to the present invention that the use of molar excesses of maleic anhydride increases the conversion of hydrocarbon to a product which is polar in nature and, because of the numerous anhydride groups, possesses solubility properties and physical properties which distinguishes the product from the waxy or hydrocarbon soluble succinic anhydrides described in the prior art.

The hydrocarbon starting materials for reaction with the maleic anhydride are preferably alkyl hydrocarbons and are branched or straight chained. However, the hydrocarbon chains may also contain unsaturation, aromatic rings, alkyl aromatics, and alicyclic hydrocarbon groups. For example, the hydrocarbons may contain up to about 10% by weight of alkyl aromatics. The hydrocarbon reactant in general will have less than 100 carbon atoms and such materials containing 10 to 60 carbon atoms are especially useful. As indicated, the hydrocarbon may be a crude or refined wax (soft solid) or liquid hydrocarbon. Crude wax refers to scale wax, soft wax, footsoil, slack wax, sweat wax or other waxes typically distinguished from refined waxes by their higher oil contents, lower melting points, higher penetration values and sometimes darker colors. Such waxes may be refined by conventional known processes. Refined waxes refer to the various commercial waxes including micro and macro crystalline waxes.

The reaction of the invention is carried out by charging the hydrocarbon to a well stirred reactor at atmospheric pressure and bringing to a temperature of about 130°–250° C. and more preferably 160°–190° C. Good temperature control is important since it has been found that product molecular weight tends to increase with temperature. This is because higher temperatures increase the solubilities of the wax anhydrides and they are thus more likely to have another anhydride unit attach. Thus, narrow temperature control tends to yield more uniform products with respect to the average number of anhydride groups attached to the hydrocarbon. Further, temperatures below 160° C. tend to favor formation of oligomers of maleic anhydride. U.S. Pat. No. 4,212,788 teaches that 120° to 145° C. is a good temperature range for producing polymaleic anhydride. The reaction should be conducted under an inert atmosphere for best results. The molten neat anhydride, preferably maleic anhydride, is then added to the hydrocarbon in a dropwise manner until the addition is complete. A free radical generator is added dropwise during the maleic anhydride addition. Any of the known numerous free radical generators may be used, in particular peroxides and hydroperoxides. Suitable free-radical generators include, for example, benzoyl peroxide, acetyl peroxide, 2,4-dichlorobenzoyl peroxide, tert-butyl peroxide, tert-butyl hydroperoxide, methyl benzyl hydroperoxide, cumene hydroperoxide, peracetic acid, tert-butyl permaleic acid, lauryl peroxide, methyl ethyl ketone peroxide, dicumyl peroxide, di-tert-butyl diperphthalate, tert-butyl peracetate, decanoyl peroxide, and the like.

Other sources of free radicals besides peroxides can also be employed, for example, high energy ionizing irradiation, etc., cobalt in conjunction with hydroperoxides, inorganic peroxy compounds such as persulfates, hydrogen peroxide, etc., azo compounds of the general formula R—N=N—R such as azobenzene, azomethane and the like. Di-t-butyl peroxide is particularly useful for the invention because of its decomposition-temperature relationship. The amount of free radical generator used should range from about 5-15% by weight based on the amount of anhydride used in the reaction.

In an alternative procedure, the anhydride and free radical initiator may be initially charged to the reactor together with the hydrocarbon instead of adding the anhydride and initiator dropwise. The mixture would then be heated at 130°-250° until reaction was complete. The dropwise addition of the anhydride and free radical generator, however, has been found preferable since it provides higher yields and products which are lighter in color. Also, dropwise addition tends to reduce unreacted maleic anhydride and its oligomers in the product. Too rapid an addition rate can lead to the aforementioned problems. The addition rate can be increased if the lower phase crude product is periodically or continuously removed from the reactor and this is a preferred mode of operation. The reason for this is believed to be that the maleic anhydride is more soluble in the hydrocarbyl anhydride phase, and its increased concentration increases the probability of forming oligomers.

The anhydride and peroxide initiator are typically added over a period of 1 to 3 hours to stirred hydrocarbon maintained within a chosen 5° C. range. Obviously higher volumes would require longer addition times. The addition is then followed by a period of additional stirring and heating, such as 1 to 2 hours for a typical reaction. The stirring and heating are then discontinued, whereupon the crude product settles to the bottom of the reactor leaving molten wax and wax-soluble anhydrides as an upper layer. This waxy upper layer may be decanted and is suitable for recycle with fresh wax in subsequent batch reactions. The lower phase will be found to harden and may then be ground and extracted with hexane or other aliphatic hydrocarbon to remove wax and wax soluble components. This yields the preferred alkyl polysuccinic anhydride of the invention in the form of a fine powder which may be melted and flaked if desired.

The products of the present invention may be made by either the batch or continuous processing methods. In continuous processing methods, the crude polyanhydride will be allowed to settle to the bottom of a quiescent zone inside or connected to the reactor. The crude product is withdrawn and balanced with fresh and/or recycle material feed. Aliphatic hydrocarbon extraction of the crude product will lead to the desired result plus a hydrocarbon solution of feed hydrocarbon and aliphatic hydrocarbon soluble anhydrides. Stripping of the aliphatic hydrocarbon yields the feed hydrocarbon plus anhydride which may then be recycled if desired.

Oligomers of maleic anhydride may be a by-product under certain reaction conditions. These can be practically eliminated by operating under the preferred embodiments discussed within this disclosure. Maleic anhydride oligomers are indicated present in products where their infrared spectra have an absorption between 1847-1857 CM-1 and they often form precipitates, sodium salts, from 10% aqueous sodium hydroxide at about 25% weight concentration. These oligomers may often be indicated present by x-ray powder diffraction analyses and carbon nuclei magnetic resonance methods. The preferred products of this invention have an infrared spectra absorption between 1857 and 1863 CM-1, yield clear solutions in 10% sodium hydroxide at the 25 weight percent level or higher, and generally produce x-ray diffraction patterns consisting of a broad hump void of sharp peaks in the range from 6 to 33 (2 theta, D spacing—14.718 to 2.712 angstroms).

As indicated above, the products of the invention may be used as dispersants in formulation of an aqueous based hydraulic fluid which will also typically contain an oil, anti-wear additives, and corrosion inhibitors. Particularly preferred formulations of such hydraulic fluids comprise the following:

| Component | Amounts |
| --- | --- |
| Dispersant | 10-20 wt. % |
| Surfactant | 15-30 wt. % |
| Corrosion inhibitors | 5-30 wt. % |
| Water | Balance |

In the above formulation, the dispersant, which is preferably present in an amount of about 12-16%, will be the alkyl poly(anhydrides) of this invention. The surfactant which is preferably present in amounts of about 18-22%, is most preferably a polyethoxylated octylphenol product which is available from the Rohm & Haas Company under the tradename "Triton" and particularly "Triton X-100". Preferred corrosion inhibitors include copper corrosion inhibitors as well as amines. The copper corrosion inhibitors are preferably present in amounts of about 7 to 10% and are particularly suitable when the hydraulic fluid is used with bearings which contain copper alloys. Satisfactory copper corrosion inhibitors include sodium mercaptobenzothiozoles which are available from the R. T. Vanderbilt Corporation under the tradename "Nacap". Particularly preferred amines which are useful as vapor phase corrosion inhibitors, that is which inhibit corrosion just above the surface of the fluid, include diethanolamine, monoethanolamine, dimethylethanolamine, morpholine, and other known amine corrosion inhibitors.

The composition may also contain anti-wear additives such as zinc dialkyldithiophosphate, sold by The Lubrizol Corporation for this purpose, an anti-foam agent such as Foam Ban MS-30 sold by Ultra Adhesive Corporation, and various other known additives for such hydraulic fluids, depending on the ultimate use. The remainder of the composition will comprise water which is present in amounts which are not considered critical, but which may range from 20 to 80% by weight.

Aqueous based hydraulic fluids produced from the above formulation and using the dispersants of the invention were found to be stable in water of extreme hardness. Water of extreme hardness is defined herein as containing at least 1500 ppm of calcium carbonate.

The products of the present invention are also useful as curing agents for epoxy resins. As a curing agent, the polyanhydrides are preferably present in amounts of about 30–50% of the weight of the epoxy resin to be cured. The products of the present invention may be milled with the resin and/or melt blended. Alternatively, the products may be mixed, dissolved, slurried, or made into a paste or gel by combining with commercially available liquid or solid anhydrides or diluents. Non-limiting examples include anhydrides that may be combined with the products of this invention such as Azcure 910 and Azcure 911 (AZS Corporation), dodecenyl succinic anhydride, methyl tetrahydrophthalic anhydride, methyl hexahydrophthalic anhydride, hexahydrophthalic anhydride, tetrahydrophthalic anhydride, benzophenone tetracarboxylic dianhydride, phthalic anhydride, nadic methyl anhydride, methyl himic anhydride, polysebacic poly anhydride, polyadipic poly anhydride, polyazelaic poly anhydride, AC-methyl, AC-32, AC-34, and AC-39 (Anhydrides and Chemicals, Incorporated). An especially preferred reactive diluent to combine with the products of this invention is gamma-butyrolactone.

The following examples are presented to illustrate the invention but it is not to be considered as limited thereto. In the examples and throughout the specification, parts are by weight unless otherwise indicated.

EXAMPLES 1 TO 9

In the following examples, a resin kettle was prepared equipped with an addition funnel for addition of maleic anhydride. Further, a mechanical stirring assembly and a small diameter tube for the peroxide initiator was prepared. This reactor was charged with the hydrocarbon feed. The hydrocarbon was then heated by means of an external electric heating mantle up to the reaction temperature, which was generally about 180° C. The dropwise addition of molten maleic anhydride was initiated and at the same time, peroxide dropwise addition was started. The peroxide was delivered by means of a syringe pump attached to the small bore inlet tube and added at a rate so that addition ended at nearly the same time the maleic anhydride addition ended. The hydrocarbon was well stirred throughout the addition and kept under a nitrogen atmosphere. At the end of the addition, heating and stirring were continued for an additional 1 to 2 hours. Heating and stirring were then stopped. Depending upon the maleic anhydride to hydrocarbon ratio used, either a single or dual phased crude product resulted. In the case of the two phase crude product, the upper phase was predominantly hydrocarbon and easily decanted from the lower phase material. The lower phase material hardened upon cooling. This crude material was ground in the presence of hexane, the slurry heated to reflux and allowed to settle. The bulk of the upper liquid phase was removed and fresh hexane makeup added. The heating, settling, and hexane removal steps were repeated one more time. The product was then readily isolated by filtration and vacuum dried to yield a fine powder. The powder could generally be melted and flaked.

A single phase crude product was treated by the same workup procedure used for the lower phase of a two phase crude product. A preferred operation is to periodically remove lower phase material from the reactor during a run. This may be done by means of a valve on the bottom of the reactor or a suction line extending to the inside bottom of the reactor. It may be necessary to shut off stirring for a few minutes to allow settling of the lower phase material. This may not be necessary in cases where the stirring paddle is near the liquid surface, creating a relative quiescent zone at the bottom of the reactor. Fresh and/or recycled hydrocarbon may be added to the reactor to replace the crude lower phase material removed. If an aqueous product is desired, an alternative workup procedure may be advantageous over the hexane extraction operation. For example, the crude product may be heated and stirred in water. Some filtration or extraction with hydrocarbon solvent may be necessary if clear solutions are desired. This workup, of course, yields carboxylic acids instead of anhydrides. Additional components may be added at any point during this aqueous workup to yield hydraulic fluid formulations.

By infrared analyses, the products showed characteristic anhydrided absorptions at 1780–1782 and 1857–1861 wave numbers (cm−1) and little evidence of residual maleic anhydride. The flaking operation did cause slight (2–5%) weight loss attributable to residual maleic anhydride. The products were submitted to gel phase chromatography to determine average molecular weights and also titrated for total acid number, which is defined as milligrams KOH per gram of sample. The average number of anhydride groups per molecule was calculated from the number average molecular weight and the acid number. The hexane solutions from the extractions could be stripped yielding hydrocarbon plus hydrocarbon-soluble anhydrides. This mixture could be recycled in subsequent reactions with no apparent problems.

Table 1 following presents experimental data on these examples and the products made by the general procedures described above. In Table 1, Examples 3, 4 and 5 demonstrate the reproducibility of preparing polyanhydrides from HSW, which is a heavy soft wax or unrefined wax comprising a complex mixture of hydrocarbons. A typical HSW would be 93% saturates and 7% alkyl aromatics as defined by ASTM D-207. The saturates would be predominantly branched paraffins with up to 35% linear paraffins and a small amount of cyclic paraffins. HSW has an oil content of up to 20%. It will be noted that the product yield and properties reproduced well. It will also be noted that there are variations in the relative quantities of upper and lower phase crude products since these are a function of physically separating the two layers, which was difficult to reproduce on a small scale. Example 6 demonstrates the feasibility of recycling material extracted from previous crude products, Example 8 demonstrates the preparation of a polyanhydride from a refined wax, Example 9 demonstrates the applicability of the invention to liquid hydrocarbons.

In Table 1 it will be noted that various abbreviations are used, which are defined as follows:

HC=Hydrocarbon  HSW=Heavy Soft Wax
MA=Maleic Anhydride  DTBP=Di-t-Butyl Peroxide
TAN=Total Acid Number (mg KOH/Gram Sample)
GPC=Gel Phase Chromatography (No. Avg. Mol. Weight)
AGPM=Anhydride Groups per Molecule
LSW=Light Soft Wax BSW=Blended Soft Wax (light, medium, and heavy)
Note: light, medium, and heavy refer only to relative molecular weights.

TABLE 1

| Run Example Number | 1 | 2 | 3 | 4 | 5 | 6 | 7 | 8 | 9 |
|---|---|---|---|---|---|---|---|---|---|
| HC Feed Description | BSW | HSW | HSW | HSW | HSW | RECYCLE FROM 3-5 | LSW | 125 F WAX REFINED | DODECANE |
| HC MOLECULAR WEIGHT (GPC) | 278 | 610 | 610 | 610 | 610 | — | 316 | 474 | 170 |
| HC CHARGE, GRAMS | 200 | 51 | 456 | 456 | 456 | 456 | 200 | 300 | 72 |
| MA, GRAMS | 300 | 40 | 125 | 125 | 125 | 120 | 300 | 250 | 63 |
| MOL RATIO, MA/HC | 4.3 | 4.9 | 1.7 | 1.7 | 1.7 | 2.0 (2) | 4.8 | 4.0 | 1.5 |
| DTBP, GRAMS | 29 | 4 | 12 | 12 | 12 | 11 | 29 | 24 | 6 |
| TOTAL RUN TIME, HRS | 3.3 | 2.8 | 5.0 | 5.0 | 5.0 | 5.0 | 3.3 | 6.0 | 3.5 |
| MAX. TEMP., C. | 187 | 198 | 182 | 184 | 182 | 183 | 185 | 190 | 182 |
| DECANTED UPPER PHASE, GRAMS | 5 | 0 | 311 | 180 | 316 | 251 | 24 | 0 | 53 |
| LOWER PHASE, GRAMS | 495 | 91 | 268 | 301 | 260 | 314 | 472 | 560 | 79 |
| TOTAL MASS ACCOUNTABILITY, | 94 | 96 | 98 | 98 | 97 | 96 | 94 | 98 | 94 |
| HEXANE EXTRACTION | | | | | | | | | |
| 1st Extract, Wt. % | 12 | 35 | 17 | 21 | 21 | 19 | 10 | 20 | 3 |
| 2nd Extract, Wt. % | 5 | 7 | 15 | 20 | 17 | 13 | 4 | 8 | 0 |
| Dried Polyanhydride, Wt. % | 79 | 54 | 66 | 57 | 62 | 67 | 85 | 74 | 76 |
| POLYANHYDRIDE YIELD, % (1) | 74 | 52 | 30 | 29 | 28 | 36 | 76 | 75 | 49 |
| POLYANHYDRIDE TAN | 601 | 586 | 477 | 457 | 474 | 478 | 587 | 601 | 641 |
| POLYANHYDRIDE MW (GPC) | 825 | 1264 | 1300 | 1310 | 1330 | 1256 | 846 | 942 | 458 |
| CALC. AVG. AGPM | | | | | | | | | |
| BASED ON TAN | 3.1 | 6.6 | 4.5 | 4.1 | 4.4 | 4.5 | 3.4 | 5.4 | 2.2 |
| BASED ON GPC | 5.5 | 6.6 | 7.0 | 7.2 | 7.3 | 6.5 | 5.4 | 4.7 | 2.9 |

NOTES
(1) Yield % = (Total Dried Polyanhydride Wt.)/(MA + HC + Peroxide) Total Weight × 100%
(2) Includes Anhydride Incorporated in Recycled Feed.

EXAMPLE 10

The polyanhydride products produced in Table 1 are also found to perform satisfactorily as dispersants in high water content hydraulic fluid formulations. A suitable aqueous based hydraulic fluid is as follows:

| Component | Amounts |
|---|---|
| Dispersant | 14 wt. % |
| Surfactant | 20 wt. % |
| Copper corrosion inhibitors | 8.6 wt. % |
| Amines | 20.4 wt. % |
| Water | 37% |

In the above formulation, the surfactant in all cases in Triton X100, which is a polyethoxylated octylphenol. The copper corrosion inhibitor is Nacap, which is sold by the R. T. Vanderbilt Corporation as a tradename for sodium mercaptobenzothiozole. The amines, which are vapor phase corrosion inhibitors, are diethanolamine, monoethanolamine, and morpholine.

The aqueous based hydraulic fluid was stable in water of extreme hardness, that is, containing up to 1500 ppm of calcium carbonate, for more than 7 days while operating at 70° C.

EXAMPLE 11

The products of the present invention are also useful as curing agents for epoxy resins. The following Table 2 sets forth data on cured epoxy resins made from some of the polyanhydrides recited in Table 1 and identified as such to demonstrate utility as curing agents. In Table 2, the first column designates the cured epoxy sample or run number, the second column designates the example from Table 1 for the particular polyanhydride used. The other abbreviations used are believed self-explanatory.

TABLE 2

Cured

| Epoxy Sample | Polyanhydride ID (1) and Wt. % | A/E (2) | Curing Cycle | HDT (C) (3) |
|---|---|---|---|---|
| A | 2 (Crude Product) 45 | 0.5 | 24 HRS @ 150 C | 90 |
| B | 2                   45 | 0.8 | 24 HRS @ 200 C | 122 |
| C | 3                   49 | 0.8 | 24 HRS @ 200 C | 77 |
| D | 3                   40 | 0.5 | 7 HRS @ 150 C  | 70 |
| E | 4                   31 | 0.4 | 15 HRS @ 150 C | 64 |
| F | 8                   38 | 0.6 | 15 HRS @ 150 C | 82 |
| G | DDSA (4) | — | — | 60-70 |

(1) Number corresponds to Run Number in Table 1.
(2) A/E = Anhydride/Epoxide equivalent weight ratio; the epoxide was Shell's Epon 828.
(3) Heat deflection temperature (tested under higher load than prescribed by ASTM-D648)
(4) DDSA = Commercial dodecenyl succinic anhydride (HDT value taken from 3rd Ed. of Kirk-Othmer Encyclopedia of Chemical Technology.

The invention has been described herein with reference to certain preferred embodiments. However, as obvious variations thereon will become apparent to those skilled in the art, the invention is not to be considered as limited thereto.

What is claimed is:

1. A hydrocarbyl poly(succinic anhydride) of the following formula:

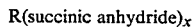

R(succinic anhydride)$_x$ wherein R is a hydrocarbyl group derived from a crude or refined hydrocarbon wax having a melting point of below 150° F., and x is an integer ranging from 3 to 8, said hydrocarbyl poly(succinic anhydride) being insoluble in the hydrocarbon wax starting material from which it is produced, the anhydride substituents being randomly located along the hydrocarbon chain, said compound being produced by reacting at least a 2:1 molar excess of maleic anhydride with said hydrocarbon wax in the presence of a free radical generator, the reaction being conducted by adding the anhydride and free radical generator to said hydrocarbon wax over a period of less than about 3 hours at a temperature of about 160° to 190° C., separating the resultant two phase product comprising an upper waxy phase and a lower hard phase and recovering the hydrocarbyl poly(succinic anhydride) product from said hard phase.

2. A method for the preparation of a hydrocarbon compound substituted with at least three succinic anhydride groups, said anhydride groups being randomly located along the hydrocarbon chain, by a process which comprises:

charging to a reactor a crude or refined hydrocarbon wax having a melting point of below about 150° F., subjecting said hydrocarbon wax to agitation at 160°–190° C. and adding thereto at least a sufficient amount of maleic anhydride to comprise at least at 2:1 molar excess of anhydride to said hydrocarbon wax, during said addition adding dropwise a free radical generator, said additions being carried out over a period of less than about 3 hours, continuing agitation after the addition is complete, separating the resultant two phase produce comprising an upper waxy phase and a lower hard phase, and recovering the hydrocarbyl poly(succinic anhydride) product from said hard phase.

3. A method according to claim 2 wherein the hydrocarbon wax is selected from the group consisting of scale wax, soft wax, footsoil, slack wax and sweat wax.

* * * * *